United States Patent
Carlyon et al.

(10) Patent No.: US 8,048,039 B2
(45) Date of Patent: Nov. 1, 2011

(54) SURGICAL FLUID TRANSFER APPARATUS

(75) Inventors: James L. Carlyon, Farmington, MO (US); David J. Salto, Hopedale, MA (US); Eugene Schrader, St. Louis, MO (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 11/904,647

(22) Filed: Sep. 28, 2007

(65) Prior Publication Data

US 2008/0082082 A1    Apr. 3, 2008

Related U.S. Application Data

(60) Provisional application No. 60/848,519, filed on Sep. 29, 2006.

(51) Int. Cl.
*A61M 5/00* (2006.01)

(52) U.S. Cl. ..... 604/246; 604/256; 604/905; 251/149.1; 251/149.6

(58) Field of Classification Search ........... 604/158, 604/164.02, 167.01, 167.02, 167.03, 167.06, 604/246, 249, 256, 537, 905, 167.04; 251/149.1, 251/149.6, 149, 149.7, 149.8, 149.9
See application file for complete search history.

(56) References Cited

U.S. PATENT DOCUMENTS

| | | | |
|---|---|---|---|
| 4,143,853 A | 3/1979 | Abramson | |
| 4,424,833 A | 1/1984 | Spector et al. | |
| 4,874,377 A | 10/1989 | Newgard et al. | |
| 4,895,346 A | 1/1990 | Steigerwald | |
| 4,909,798 A | 3/1990 | Fleischhacker et al. | |
| 4,915,687 A * | 4/1990 | Sivert | 604/83 |
| 4,917,668 A | 4/1990 | Haindl | |
| 4,960,412 A | 10/1990 | Fink | |
| 5,085,645 A | 2/1992 | Purdy et al. | |
| 5,215,538 A | 6/1993 | Larkin | |
| 5,242,393 A | 9/1993 | Brimhall et al. | |
| 5,322,518 A | 6/1994 | Schneider et al. | |
| 5,390,898 A | 2/1995 | Smedley et al. | |
| 5,535,771 A | 7/1996 | Purdy et al. | |
| 5,535,785 A | 7/1996 | Werge et al. | |
| 5,555,908 A | 9/1996 | Edwards et al. | |
| 5,573,516 A | 11/1996 | Tyner | |
| 5,578,059 A * | 11/1996 | Patzer | 604/249 |

(Continued)

OTHER PUBLICATIONS

International Search Report International Application No. PCT/US07/20987 dated May 15, 2008.

*Primary Examiner* — Kevin C Sirmons
*Assistant Examiner* — Kami A Bosworth
(74) *Attorney, Agent, or Firm* — Lisa E. Winsor, Esq.

(57) ABSTRACT

A surgical fluid transfer apparatus for passage of fluids includes a hub defining a longitudinal axis and having an internal chamber, an elongated member extending from the hub and a closure valve disposed within the internal chamber. The closure valve is adapted for movement between a first position substantially sealing the internal chamber to prevent passage of fluids and a second position establishing a fluid passage within the hub to permit passage of fluids therethrough. The closure valve includes a valve housing and a seal member. The seal member has an open condition establishing an internal passage different than the fluid passage to permit passage of an access instrument through the closure valve and a closed condition in the absence of the access instrument. The inner wall portions of the valve housing cooperate with the seal member to permit the seal member to assume the closed condition thereof.

12 Claims, 15 Drawing Sheets

U.S. PATENT DOCUMENTS

| | | |
|---|---|---|
| 5,676,346 A | 10/1997 | Leinsing |
| 5,738,144 A | 4/1998 | Rogers |
| 5,749,861 A | 5/1998 | Guala et al. |
| 5,776,113 A | 7/1998 | Daugherty et al. |
| 5,788,215 A | 8/1998 | Ryan |
| 5,806,551 A | 9/1998 | Meloul et al. |
| 5,806,831 A | 9/1998 | Paradis |
| 5,817,069 A | 10/1998 | Arnett |
| 5,954,313 A | 9/1999 | Ryan |
| 5,954,698 A | 9/1999 | Pike |
| 5,967,490 A | 10/1999 | Pike |
| 6,068,011 A | 5/2000 | Paradis |
| 6,068,617 A | 5/2000 | Richmond |
| 6,083,203 A * | 7/2000 | Yoon .................. 604/167.01 |
| 6,152,900 A | 11/2000 | Mayer |
| 6,158,458 A | 12/2000 | Ryan |
| 6,171,287 B1 | 1/2001 | Lynn et al. |
| 6,228,060 B1 | 5/2001 | Howell |
| 6,482,188 B1 | 11/2002 | Rogers et al. |
| 6,485,473 B1 | 11/2002 | Lynn |
| 6,699,221 B2 | 3/2004 | Vaillancourt |
| 6,740,063 B2 | 5/2004 | Lynn |
| 6,802,490 B2 | 10/2004 | Leinsing et al. |
| 2002/0128604 A1 * | 9/2002 | Nakajima ............. 604/164.01 |
| 2002/0147431 A1 | 10/2002 | Lopez et al. |

* cited by examiner

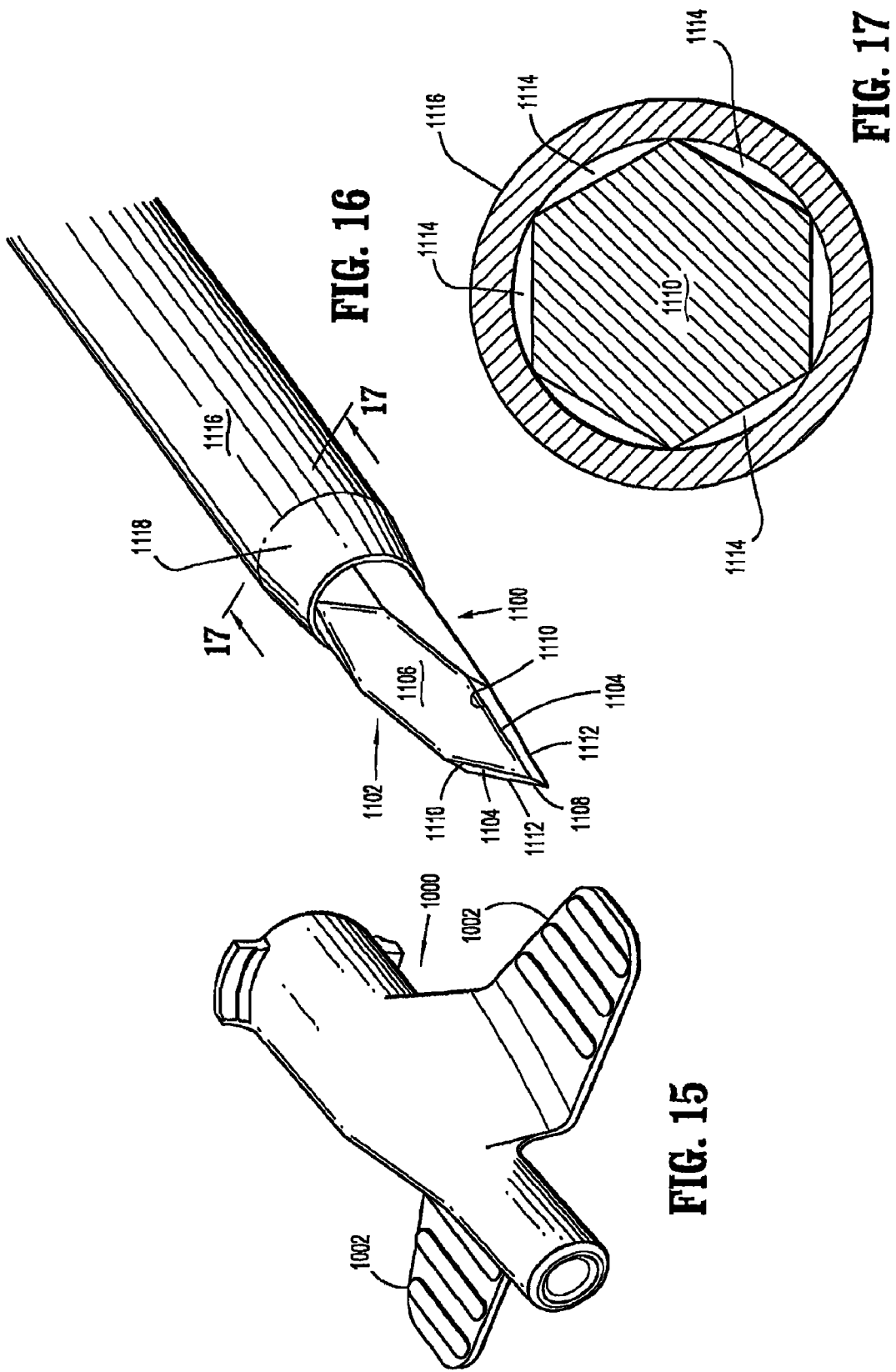

SURGICAL FLUID TRANSFER APPARATUS

CROSS-REFERENCE TO RELATED APPLICATION(S)

This patent application claims priority to and the benefit of U.S. Provisional Patent Application No. 60/848,519, filed in the U.S. Patent and Trademark Office on Sep. 29, 2006.

BACKGROUND

1. Technical Field

The present disclosure relates to the transfer of fluids in connection with a surgical procedure. In particular, the present disclosure relates to a fluid transfer apparatus having a fluid passage adapted for delivering fluids (e.g., intravenous, blood, etc) to a patient and having an improved valve mechanism permitting effective and automatic closure of the fluid passage.

2. Description of Related Art

Surgical fluid transfer instrumentation including medical catheters are widely used to withdraw or remove blood from a patient, or in combination with an intravenous system for delivering medication, plasma, etc. to the patient. In accordance with one exemplative intravenous procedure, an intravenous catheter having a needle is advanced to penetrate a vascular organ (e.g., a vein or artery). Once access to the organ is achieved, the needle is removed leaving the catheter within the organ site. A fluid distribution system (e.g., a syringe or intravenous (IV) kit) is connected to the hub of the intravenous catheter, and fluids are passed from the distribution system through the intravenous catheter to the organ site.

However, known methodologies and catheters for delivering or removing fluids are deficient for several reasons. With regard to intravenous catheters, the processes of insertion of the needle, connection of the catheter to the distribution system (e.g., syringe or IV kit) and/or disconnection of the catheter from the distribution system present difficulties for the clinician with respect to blood contamination and undesired blood transfer through the catheter hub. Such blood transfer is typically attributed to ineffective sealing about the needle during access or within the internal passageway of the catheter hub during connection or disconnection with the distribution system.

SUMMARY

Accordingly, the present disclosure overcomes the disadvantages of the prior art by providing a novel apparatus and associated methodology for the safe and effective transfer of fluids between a patient and a fluid distribution or collection system. In one preferred embodiment, a surgical fluid transfer apparatus for passage of fluids includes a hub defining a longitudinal axis and having an internal chamber, an elongated member extending from the hub and defining a longitudinal conduit and a closure valve disposed within the internal chamber of the hub. The closure valve is adapted for movement between a first position substantially sealing the internal chamber to prevent passage of fluids and a second position establishing a fluid passage within the hub to permit passage of fluids therethrough. The closure valve includes a valve housing having inner wall portions defining a general tapered internal bore and a seal member at least partially disposed within the tapered internal bore of the valve housing. The seal member defines a general tapered configuration and has an open condition permitting passage of an access instrument through the closure valve and into the longitudinal conduit of the elongated member and a closed condition in the absence of the access instrument. The inner wall portions of the valve housing cooperate with the seal member to permit the seal member to assume the closed condition thereof.

Preferably, the closure valve is adapted for longitudinal movement along the longitudinal axis between the first and second positions thereof. The closure valve may be normally biased toward the first position thereof. The first position of the closure valve may be a proximal position thereof and the second position of the closure valve may be a distal position thereof.

The seal member defines inner seal portions adapted for displacement to permit passage of the access instrument when in the open condition of the seal member and to establish a substantial sealing relation with the access instrument introduced therethrough. The seal member may be adapted for longitudinal movement relative to the valve housing between an actuated position and an initial position corresponding to the open and closed conditions of the seal member. Preferably, the inner wall portions of the valve housing defining the tapered internal bore are adapted to cooperate with the seal member upon movement of the seal member to the initial position to substantially close the inner seal portions thereof. Preferably, the actuated position of the seal member is a distal longitudinal position and the initial position is a proximal longitudinal position. The seal member may be normally biased toward the proximal longitudinal position.

The valve housing may be adapted to operatively engage an internal sealing wall of the hub when in the first position of the closure valve to substantially seal the internal chamber of the hub, and is adapted to operatively disengage the internal sealing wall when in the second position of the closure valve to establish the fluid passage. The closure valve may include a valve gasket mounted to the valve housing. The valve gasket is adapted to engage the internal sealing wall of the hub to substantially seal the internal chamber of the hub. A valve plunger may be provided proximal of the valve gasket and engageable with a connector positioned within the hub whereby advancement of the connector advances the valve plunger and the closure valve from the first position to the second position. The valve plunger may define a slot which forms part of the fluid passage. Preferably, the valve housing is mounted within the internal chamber of the hub to define a fluid space between the valve housing and an inner wall defining the internal chamber. The fluid passage incorporates the fluid space.

In another embodiment, a surgical apparatus for passage of fluids includes a hub defining a longitudinal axis, an elongated member extending distally from the hub and defining a longitudinal conduit and a closure valve mounted within the hub to define a fluid passage between the closure valve and the hub. The closure valve is adapted for longitudinal movement from a proximal position substantially closing the fluid passage to prevent passage of fluids to a distal position opening the fluid passage to permit passage of fluids through the hub. The closure valve includes a valve housing and an internal seal member mounted to the valve housing, and defining an internal passage. The internal seal member is adapted for longitudinal movement relative to the valve housing between a first position whereby the internal passage of the seal member is in a substantially closed condition and a second position whereby the internal passage of the internal seal member receives an access instrument. The seal member may be normally biased toward the first position thereof. The seal member defines a general tapered configuration and is received within a corresponding tapered internal bore of the valve housing. The seal member cooperates with wall portions of the valve housing defining the tapered internal bore upon movement of the seal member to the first position to substantially close the internal passage of the seal member.

The valve housing is adapted to engage an internal sealing wall within the hub when in the proximal position of the closure valve to close the fluid passage. The closure valve is normally biased toward the proximal position. Preferably, a spring is engageable with the internal seal member to normally bias the internal seal member to the first position corresponding to a proximal position of the internal seal member relative to the valve housing, to thereby normally bias the closure valve to the proximal position thereof. The spring may be at least partially positioned about the seal member to normally bias the seal member in a radial inward direction to facilitate formation of the substantially closed position of the internal seal member. Alternatively, the spring is integrally formed with the seal member. The spring may be generally C-shaped. The valve housing may include a valve gasket which engages the internal sealing wall when in the proximal position of the closure valve to close the fluid passage.

BRIEF DESCRIPTION OF THE DRAWINGS

Various embodiments of the present disclosure are described herein with reference to the drawings wherein:

FIG. 15 is a perspective view of an alternate embodiment of a catheter hub for use with the fluid transfer apparatus of FIG. 1;

FIG. 16 is a perspective view of the penetrating end of an insertion stylet for use with the fluid transfer apparatus of FIG. 1;

FIG. 17 is a cross-sectional view taken along the lines 17-17 of FIG. 16 illustrating the fluid channels defined between the insertion stylet and the transfer catheter;

DETAILED DESCRIPTION

The fluid transfer apparatus of the present disclosure is contemplated for medical use in distributing fluids (such as liquids including medicants, blood, plasma, saline, etc.) during an intravenous (IV) procedure, or, alternatively, in withdrawing or collecting fluids such as blood from a patient in connection with, e.g., diagnostic or circulatory assist procedures. It is contemplated that the fluid transfer apparatus may have application in any surgical procedure where fluids are transferred between a patient and an external transfer conduit or medium.

In the following description, the term "proximal" refers to the portion of the instrument closest to the clinician, while the term "distal" refers to the portion of the instrument remote from the clinician.

Figure 1:
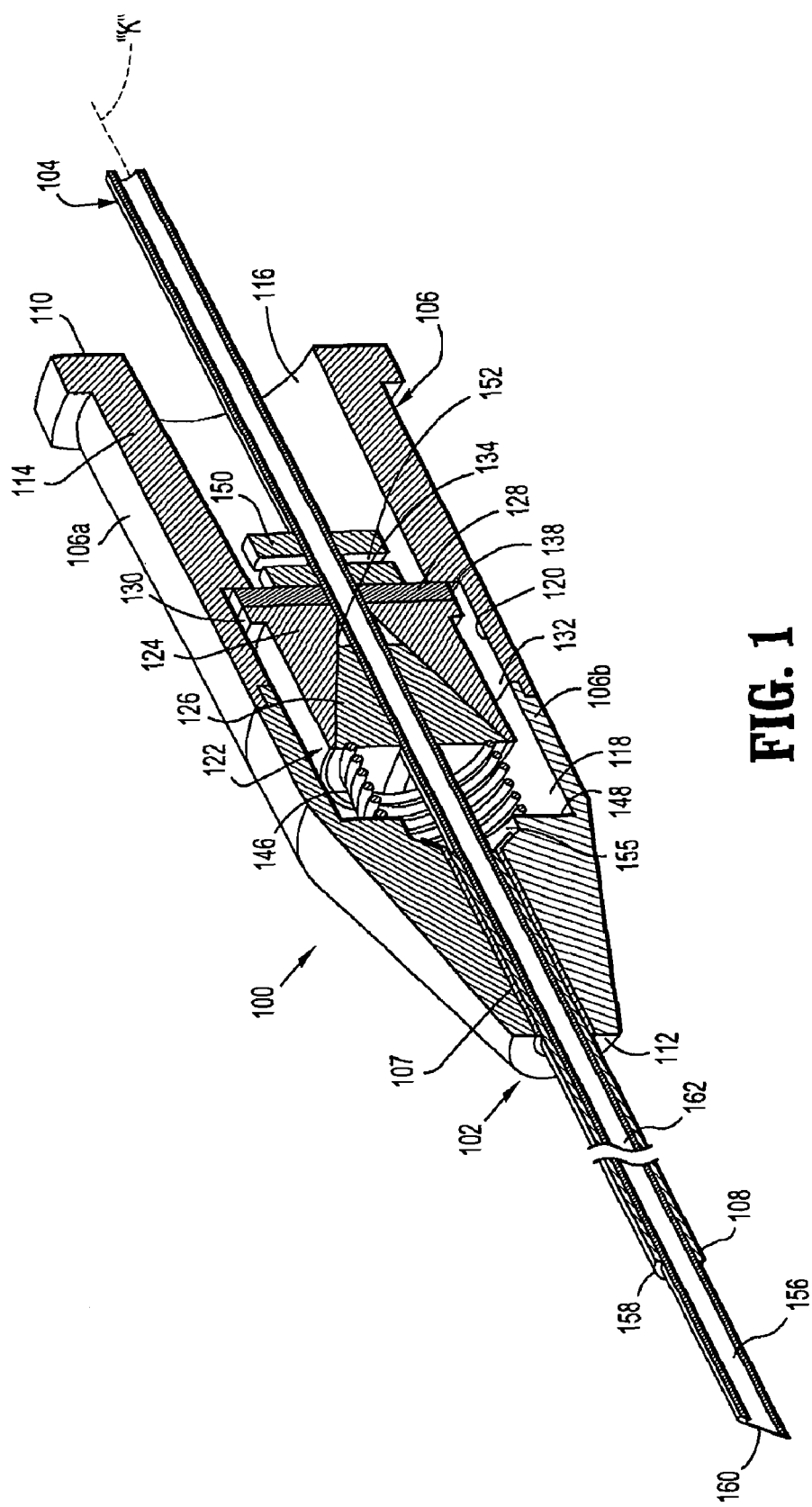
FIG. 1 is a perspective view in cross-section of the fluid transfer apparatus in accordance with the principles of the present disclosure, illustrating the transfer catheter and the access cannula positioned within the transfer catheter.

Referring now to FIG. 1, the fluid transfer apparatus 100 of the present disclosure is illustrated. Fluid transfer apparatus 100 includes transfer catheter 102 and, optionally, access cannula 104 which is positionable within the transfer catheter 102. Transfer catheter 102 includes catheter hub 106 and elongated catheter member 108 connected to the catheter hub 106 and extending distally therefrom. Catheter hub 106 defines longitudinal axis "k" and has proximal and distal ends 110, 112, respectively. Catheter hub 106 includes connector portion 114 adjacent proximal end 110 defining internal lumen 116. Internal lumen 116 is adapted to receive a connector (e.g., a luer connector) of a fluid distribution or collection system. Catheter hub 106 further includes internal chamber 118 disposed intermediate proximal and distal ends 110, 112, and defined by inner annular wall 120. Catheter hub 106 may be a single component or consist of a multitude of components assembled together (e.g., hub portions 106a, 106b and secured to each other by conventional means. Preferably, catheter hub 106 is formed of a suitable polymeric material and manufactured by conventional injection molding techniques. Catheter hub 106 may be opaque transparent or tinted. Catheter hub 106 may include legs or threads on its exterior surface to improve grasping by the surgeon. Catheter hub 106 may further incorporate winged structure to facilitate attachment to the body.

Elongated catheter member 108 may be fabricated from a biocompatible metal or polymer, and may be clear, translucent, opaque, striped. Elongated catheter member 108 may be marked with depth markings in the form of lines to assist the clinician in determining the degree of insertion within tissue.

Referring again to FIG. 1, fluid transfer apparatus 100 further includes closure valve mechanism, identified generally by reference numeral 122, at least partially disposed within internal chamber 118. Closure valve 122 performs dual functions by 1) establishing a seal about access cannula 104 when the access cannula 104 is positioned within transfer catheter 102; and 2) opening or closing a fluid passage extending through catheter hub 106 when used with a fluid distribution or collection system. Closure valve 122 includes valve housing 124, access seal member 126 at least partially positioned within the valve housing 124 and valve gasket 128. Valve housing 124 is substantially cylindrical in outer configuration along a major portion of its length, and incorporates circumferential flange 130 adjacent the proximal end of the valve housing 124. Valve housing 124 is coaxially arranged about longitudinal axis "k" within internal chamber 118 to define an annular space 132 between internal annular wall 120 of catheter hub 106 and the exterior of the valve housing 124. Annular space 132 provides a portion of the fluid passage within catheter hub 106 for passage of fluids as will be discussed.

Figure 2:
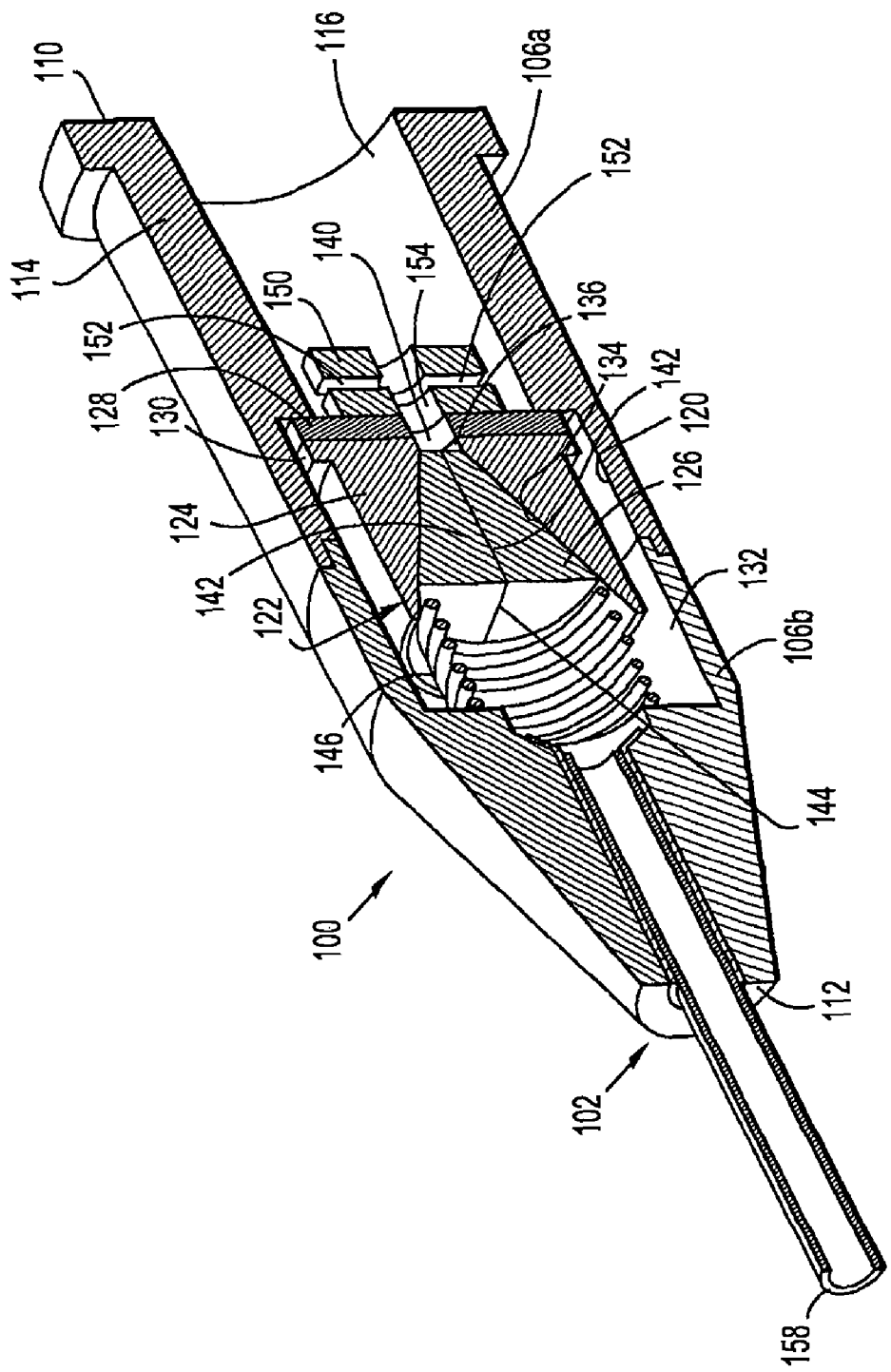
FIG. 2. is a perspective view in cross-section illustrating the transfer catheter with the access cannula withdrawn from the transfer catheter.

Referring now to FIGS. 1-2, valve housing 124 further defines tapered internal bore 134 which receives access seal member 126, and aperture 136 extending through circumferential flange 130 in communication with the tapered internal bore 134. Aperture 136 receives access cannula 104. Valve gasket 128 is mounted to the proximal end of valve housing 124. Valve gasket 128 is preferably made of a compliant material such as an elastomer, and is adapted to engage internal transverse seal wall 138 of catheter hub 106 in a manner to establish a substantially sealed relation with the internal seal wall 138. Valve gasket 128 may include aperture 140 therethrough to permit passage of access cannula 104. Valve gasket 128 may or may not form a seal about access cannula 104. It is envisioned that valve gasket 128 may have one or more slits or slots in lieu of aperture 140 to permit passage of access cannula 104. Alternatively, valve gasket 128 may be solid and pierced by access cannula 104 during passage of the access cannula 104 through catheter hub 104.

Access seal member 126 is disposed within tapered internal bore 134 of valve housing 124. Access seal member 126 preferably defines a wedge-shape or tapered configuration which generally corresponds to the tapered configuration of tapered internal bore 134. Access seal member 126 may incorporate inner seal portions 142 defining slit 144 in general alignment with aperture 140 of valve gasket 128 and with longitudinal axis "k". Inner seal portions 142 are adapted to sealingly engage access cannula 104 and to maintain a sealed relation with the access cannula 104 during insertion and removal of the access cannula 104 relative to transfer catheter 102. Access seal member 126 may be further adapted to move relative to valve housing 124 and relative to longitudinal axis "k" between an actuated distal position depicted in FIG. 1 where slit 144 may be opened and an initial proximal position as depicted in FIG. 2 where slit 144 is substantially closed. Alternatively, access seal member 126 may be generally stationary relative to valve housing 124 whereby the resilient characteristics permit the access member 126 to move between the open and closed positions. Access seal member 126 is preferably fabricated from an elastomeric material such as polyisoprene, silicone, rubber, urethane, etc. whereby the seal member 126 is adapted to open and conform to the outer dimensioning of access cannula 104. Alternatively, access seal member 126 may incorporate an expandable balloon or bladder filled with fluid, gel, foam etc., and may be reinforced with strands of fabric or other more rigid materials.

Closure valve 122 further includes spring 146 to normally bias access seal member 126 towards its closed proximal position of FIG. 2. Spring 146 preferably is a coil spring which engages, at its first or proximal end, access seal member 126, and at its second or distal end, inner bearing wall 148 of catheter hub 106. By this arrangement, spring 146 normally biases access seal member 126 in a proximal direction into tapered internal bore 134 of valve housing 124. As access seal member 126 is driven into tapered internal bore 134, the tapered configurations of the wall portions defining tapered internal bore 134 and access seal member 126 cooperated to close slit 144. In addition, as appreciated, proximal biasing of access seal member 126 also serves to bias valve housing 124 and valve gasket 128 towards the first proximal position shown in FIG. 2.

Closure valve 122 further includes valve plunger 150 attached to the proximal side of valve gasket 128. Valve plunger 150 may be integrally formed with valve housing 124 extending through an opening in valve gasket 128 or may be a separate component attached to the peripheral area of the valve gasket 128 by conventional means. Valve plunger 150 incorporates a slot 152 in its outer wall which communicates with central aperture 154 of the valve plunger 150. Slot 152 and central aperture 154 provide a fluid path for fluid, e.g., blood or therapeutic fluids, to pass to the luer connector.

Referring still to FIGS. 1 and 2, elongated member 108 of transfer catheter 102 may be connected to catheter hub 106 through any conventional means including adhesives, cements, interference fits, couplings etc. In one preferred arrangement, hub portion 106b includes or defines a ferrule 107 to connect elongated member 108 to catheter hub 106. Ferrule 107 may be secured within hub portion 106b through conventional means and may have elongated member 108 connected thereto. Ferrule 107 and/or elongated member 108 may have a flange which resides within recess 155 of catheter hub 106. The flange may be cemented within recess 155. Elongated member 108 defines longitudinal conduit 156 therethrough which provides a fluid passage through the elongated member 108 and in communication with internal chamber 118 of catheter hub 106. Elongated member 108 may be rigid or flexible, and may be linear or incorporate a curved section. Elongated member 108 may have open distal end 158 which is preferably blunt or have a beveled arrangement. Elongated member 108 may comprise steel or a polymeric material.

Referring now to FIG. 1, access cannula 104 of fluid transfer apparatus 100 will be discussed. Access cannula 104 may be any conventional access cannula or needle suitable for the intended purpose of accessing a blood vessel to facilitate introduction of transfer catheter 102. Access cannula 104 may have sharp end 160 to pierce and penetrate the vascular wall and may define longitudinal conduit 162. Access cannula 104 preferably has a housing or hub (not shown) mounted to the proximal end of access cannula 104. Access cannula 104 may include stop (not shown) mounted about an intermediate portion of the access cannula 104 to control the degree or amount of insertion of the access cannula 104 relative to transfer catheter 102. Stop may be positioned on access cannula 104 to contact valve plunger 150 or engage proximal end 110 of hub 106. In the alternative, access cannula 104 may be replaced with a solid stylet or guidewire or any other access instrument intended to facilitate access to the blood vessel. Once access to the blood vessel is achieved with access cannula 104, the access cannula 104 is removed from transfer catheter 102.

The use and function of fluid transfer apparatus 100 will now be described in the context of accessing a blood vessel for the introduction of IV fluids. With reference to FIG. 1, access cannula 104 is positioned within transfer catheter 102. During introduction of access cannula 104, the access cannula 104 passes through aperture 140 of valve gasket 128 to engage access seal member 126. Upon engagement with access seal member 126, access cannula 104 moves the access seal member 126 in a longitudinal direction within tapered internal bore 134 of valve housing 124 from the initial proximal position depicted in FIG. 2 to the actuated distal position depicted in FIG. 1. As access seal member 126 moves distally within valve housing 124, slit 144 of the access seal member 126 is permitted to open via the cooperating tapered configurations of the access seal member 126 and tapered internal bore 134 to permit passage of access cannula 104 through the access seal member 126 and through elongated member 108 of transfer catheter 102. If provided, a stop located on access cannula 104 may limits the degree of insertion of access cannula 104 within transfer catheter 102. With access cannula 104 assembled within transfer catheter 102 as shown in FIG. 1, the access cannula 104 is used to penetrate a blood vessel as is known in the art. Upon entry into the blood vessel, blood passes through longitudinal conduit 162 of access cannula 104 to a proximal location where the presence of blood in the access hub or housing (not shown) indicates to the clinician that the blood vessel has been accessed. Access cannula 104 is advanced until distal end 160 of elongated member 108 of transfer catheter 108 is positioned within the blood vessel. As indicated above, access seal member 126 establishes a fluid tight seal about access cannula 104 substantially preventing any fluids, e.g., blood, from passing along the outer surface of the access cannula 104 and through the hub 106.

Referring now to FIG. 2, access cannula 104 is withdrawn from transfer catheter 102 leaving the transfer catheter 102 within the blood vessel. During removal of access cannula 104, access seal member 126 maintains a fluid tight seal about the access cannula 104 thereby substantially preventing any body fluids from passing about the outer surface of the access cannula 104. With access cannula 104 removed, access seal member 126 returns to the initial proximal position depicted in FIG. 2 under the influence of coil spring 146. As access seal member 126 moves in a proximal direction, the corresponding tapered configurations of access seal member 126 and tapered internal bore 134 of valve housing 124 cooperate to close slit 144 of the access seal member 126. In addition, proximal movement of access seal member 126 will also drive valve housing 124 and valve gasket 128 in the proximal direction with the valve gasket 128 sealingly engaging internal seal wall 138 of catheter hub 106. Thus, in the condition of closure valve 122 as depicted in FIG. 2, fluid is not capable a passing through catheter hub 106.

Figure 3:
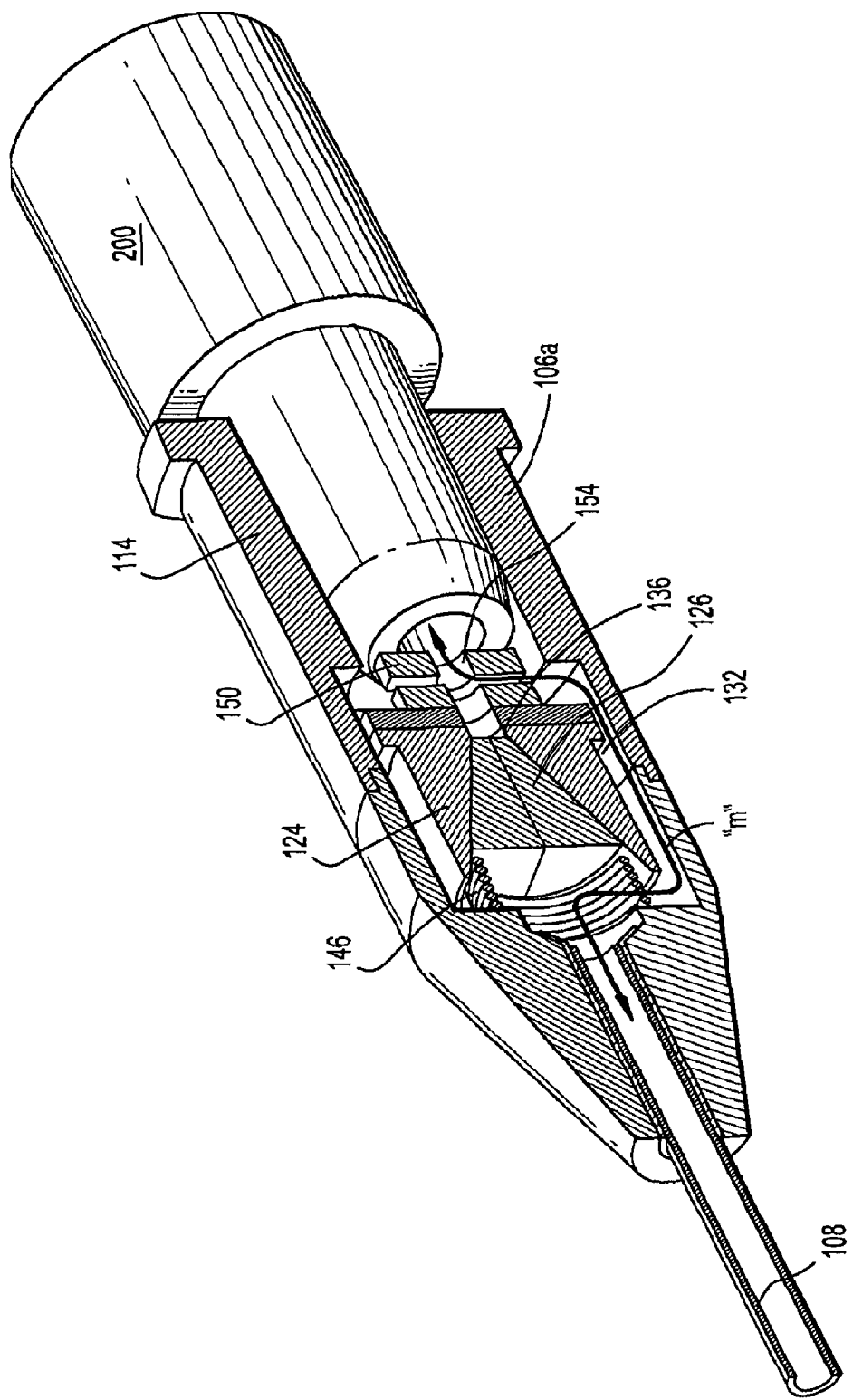
FIG. 3 is a perspective view in cross-section illustrating a connector of a fluid distribution or collection system mounted to the transfer catheter.

Referring now to FIG. 3, luer connector 200 of an IV system is advanced within the internal bore 116 of connecting portion 114 of catheter hub 106 to establish a coupled relation with the catheter hub 106. As luer connector 200 moves distally within catheter 106, valve plunger 150 adjacent valve gasket 128 is engaged by the connector 200 to thereby drive closure valve 122 against the bias of spring 146 from the first proximal position depicted in FIG. 2 to the second distal position depicted in FIG. 3. In the second distal position of closure valve 122, valve gasket 128 is disengaged from internal seal wall 138 thereby establishing a fluid passage through catheter hub 106. Accordingly, fluids may be transferred between connector 200 and longitudinal conduit 150 of elongate member 108 via the established fluid passage which is inclusive of annular space 132 and the proximal portion of internal chamber 118. The fluid may pass between connector 200, through central aperture 154 and slot 152 of valve plunger 150. The fluid passage is identified by the directional arrows "m" in FIG. 3. It is noted that in this position access seal member 126 remains closed. When the procedure is completed, connector 200 is removed and closure valve 106 is driven proximally under the influence of spring 146 to the position of FIG. 2 thereby closing the fluid passage "m".

Figure 4:
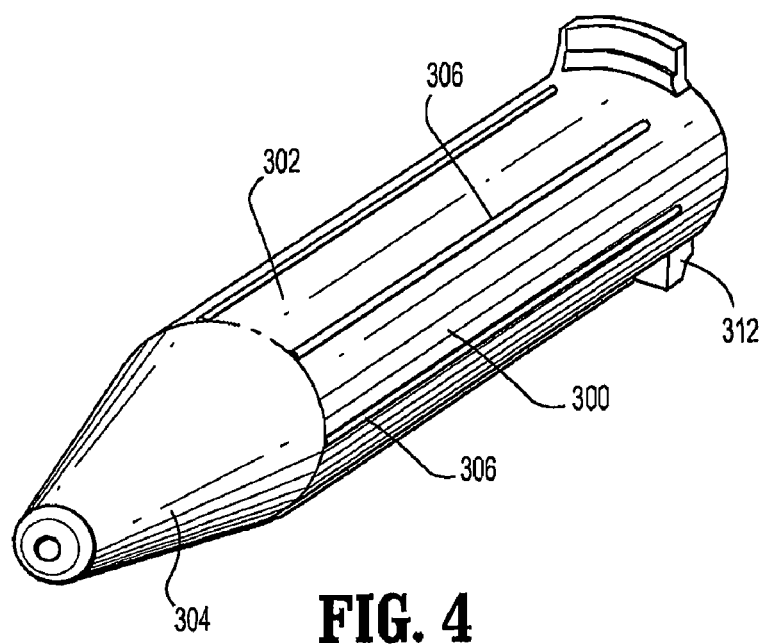
FIG. 4 is a perspective view of an alternate embodiment of a catheter hub of the transfer catheter.
Figure 5:
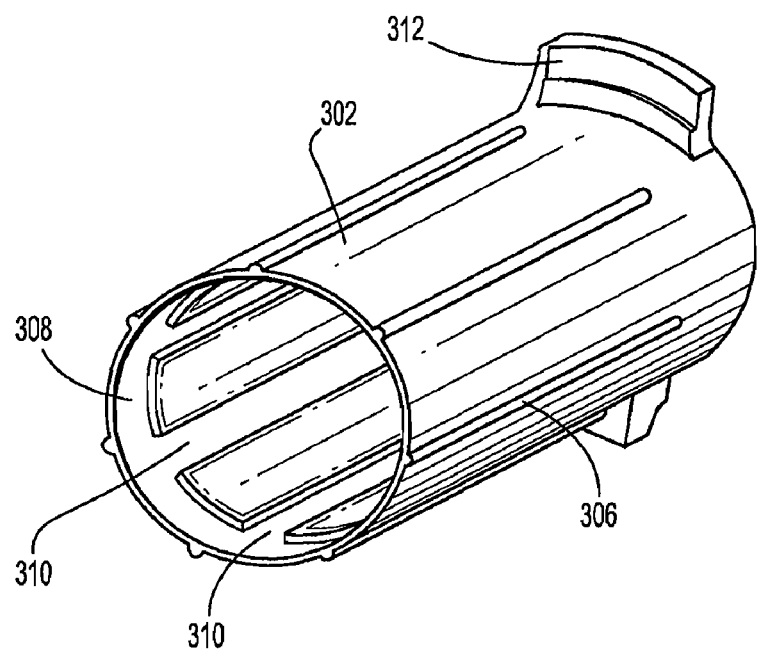
FIG. 5 is a perspective view of the proximal hub portion of the catheter hub of FIG. 4.

FIGS. 4-5 illustrates an alternate embodiment of catheter hub 106. In accordance with this embodiment, catheter hub 300 includes hub portions 302, 304, assembled together, via conventional means including, e.g., adhesives or the like. Hub portion 302 includes external axial ribs 306 which facilitate engagement by the clinician. Inner annular wall 308 includes recessed channels 310 extending in a general longitudinal direction. Recessed channels 310 permit flow of fluids within catheter hub 302 i.e., recessed channels 310 define in part, or in its entirety, the fluid passages about closure valve 122 and within catheter hub 300. Catheter hub 300 further includes threads or lugs 312 on its external surface which provides positive retention of a luer connector, i.e., by cooperatively engaging corresponding structure on the luer connector 200.

Figure 6:
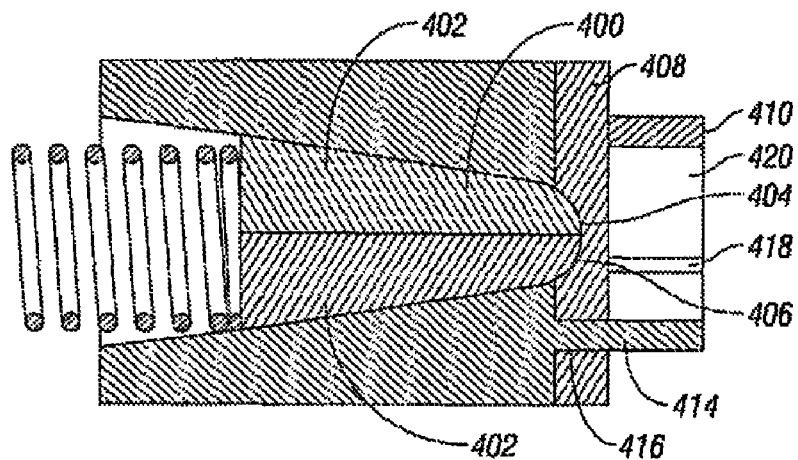
FIG. 6 is a side cross-sectional view of another alternate embodiment of the closure valve of the transfer catheter.
Figure 7:
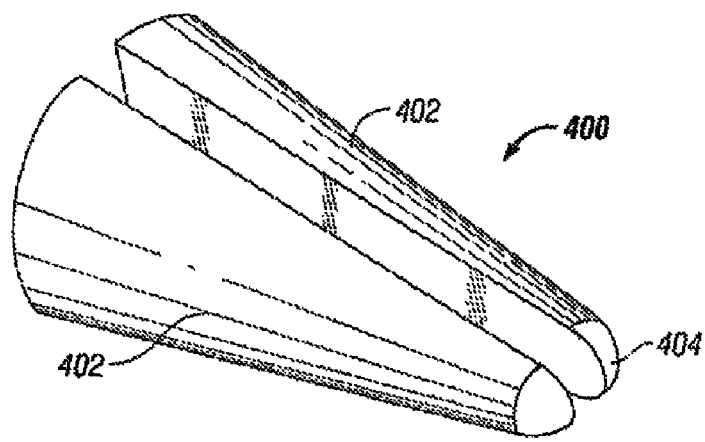
FIG. 7 is a perspective view of the access seal member of the closure valve of FIG. 6.

FIGS. 6-7 illustrate an alternate embodiment of the present disclosure. In accordance with this embodiment, access seal member 400 includes a plurality of separate components, e.g., two wedge pieces 402, arranged to define a general wedge shaped arrangement. Access seal member 400 further defines an arcuate or bullet shaped nose 404. Nose 404 resides within a corresponding recess 406 of valve gasket 408. As shown, valve plunger 410 is integrally formed with valve housing 412, preferably, monolithically formed, via connector rib 414 extending through a corresponding aperture 416 of valve gasket 408. Valve plunger 410 further defines axial slot 418 in communication with lumen 420 to provide a fluid path into the opening of luer connector 200.

Figure 8:
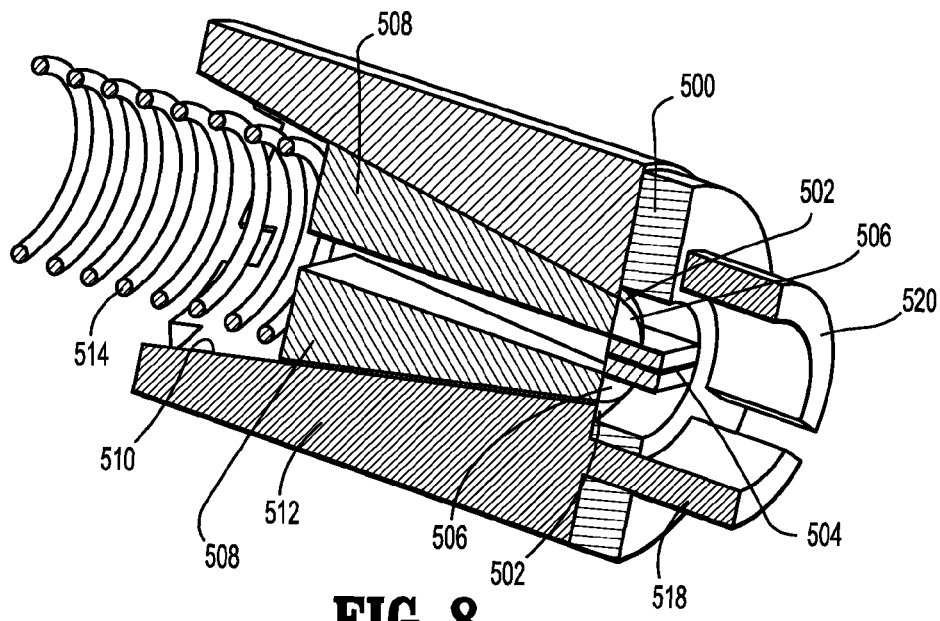
FIG. 8 is a perspective view in cross-section of another alternate embodiment of the closure valve of the transfer catheter.
Figure 9:
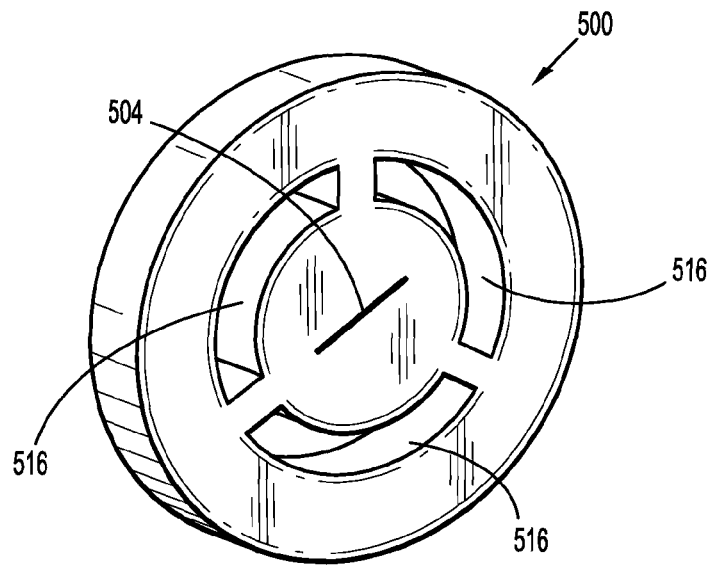
FIG. 9 is a perspective view of the valve gasket of the closure valve of FIG. 8.

FIGS. 8-9 illustrate an alternate embodiment substantially similar to the embodiment of FIGS. 6-7. However, valve gasket 500 defines opposed arcuate recesses 502 surrounding valve slit or opening 504 as best depicted in FIG. 8. Recesses 502 receive the nose sections 506 of internal seal member 508. With this arrangement, nose section 506 of internal seal member 508 serve to facilitate closure of opening 504 of valve gasket 500 by virtue of the corresponding tapered configurations of internal seal member 508 and internal wall 510 of valve housing 512, and the proximal bias of coil spring 514. Thus, with this arrangement, either valve gasket or internal seal member 508, or both, may form a fluid tight seal about access cannula 104. In addition, valve gasket 500 may serve to close the path through the catheter hub. FIG. 9 illustrates further features of valve gasket 500. Specifically, valve gasket 500 further includes three arc section or openings 516 which accommodate rib portions 518 of valve plunger 520. Valve plunger 520 connects to valve housing 512.

Figure 10:
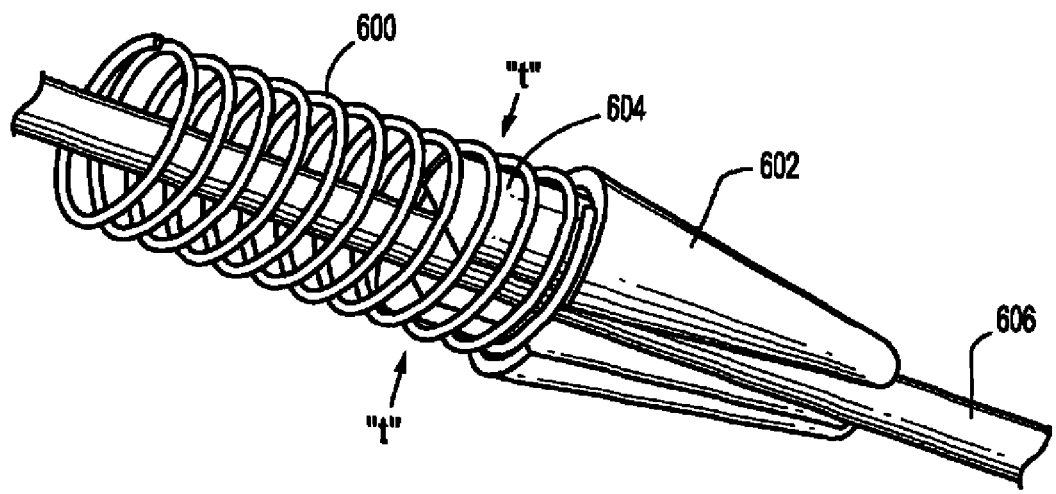
FIG. 10 is a perspective view of an alternate coil spring and access seal member for use with the transfer catheter.

FIG. 10 illustrates an alternate embodiment in which coil spring 600, instead of contacting the distal side of access seal member 602, is at least partially positioned about reduced cylindrical portion 604 of the access seal member 602. Accordingly, coil spring 600 serves to both normally bias access seal member 602 in a proximal direction while also applying a radial inward force "t" to reduced cylindrical section 604 thereby normally biasing the access seal member 602 radially inwardly in substantial sealed selection with access cannula 606.

Figure 11:
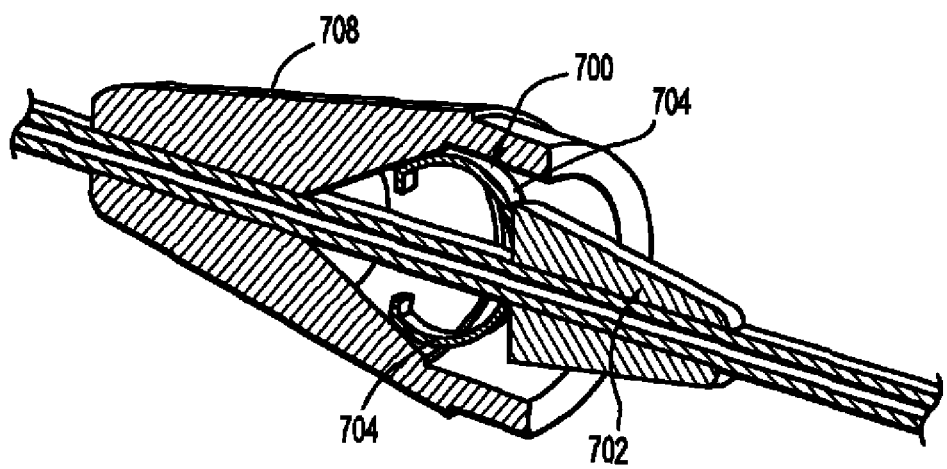
FIG. 11 is a perspective view in cross-section of another alternate embodiment of the closure valve.

FIG. 11 illustrates another embodiment where in lieu of a coil spring, a C-shaped spring 700 is provided. C-shaped spring 700 is preferably integrally formed with access seal member 702. Legs 704 of C-shaped spring 700 engage inner tapered wall 706 of distal hub portion 708. Inner tapered wall 706 cooperates with legs 704 to normally bias access seal member in a proximal direction into the tapered bore (not shown) of valve housing (not shown) to seal the apparatus in a similar manner discussed hereinabove in connection with the embodiment of FIGS. 1-3.

Figure 12A:
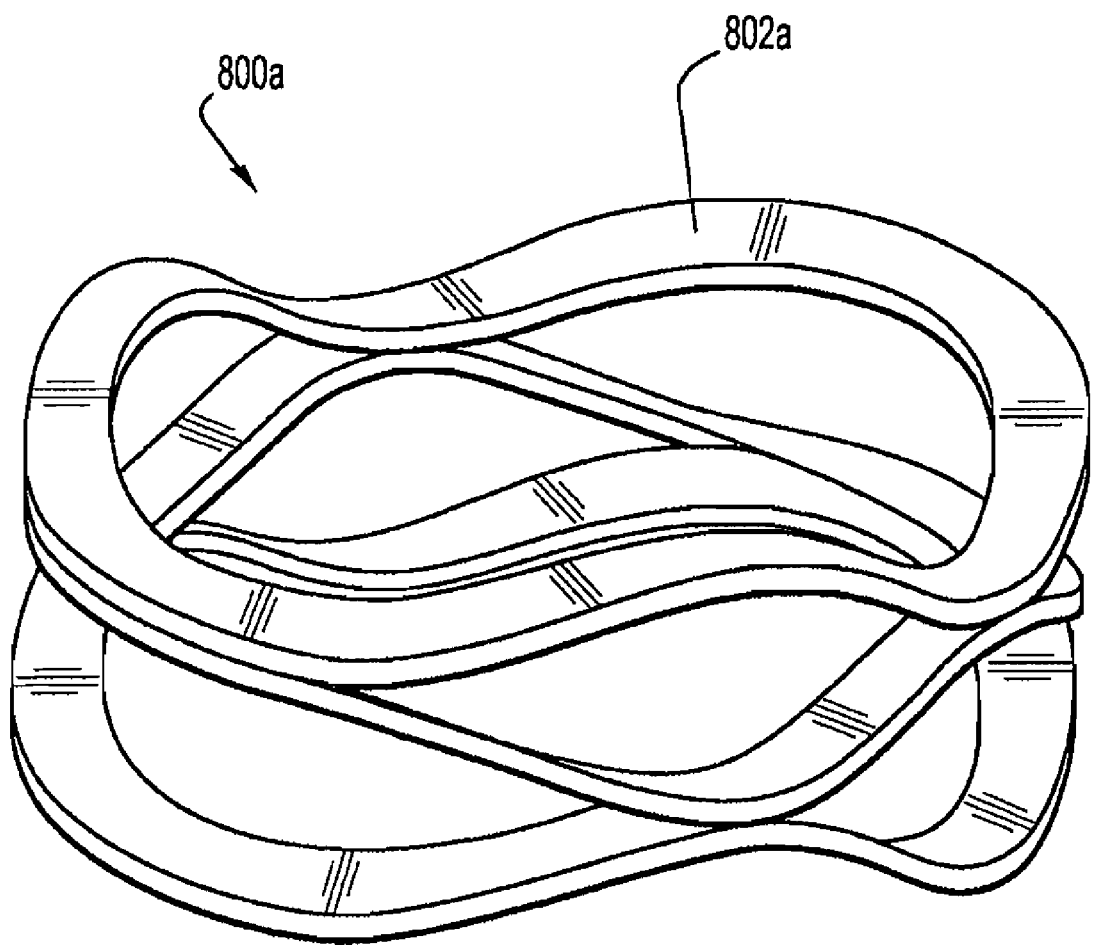
FIGS. 12A-12B are perspective views of alternate springs for use with the closure valve.
Figure 12B:
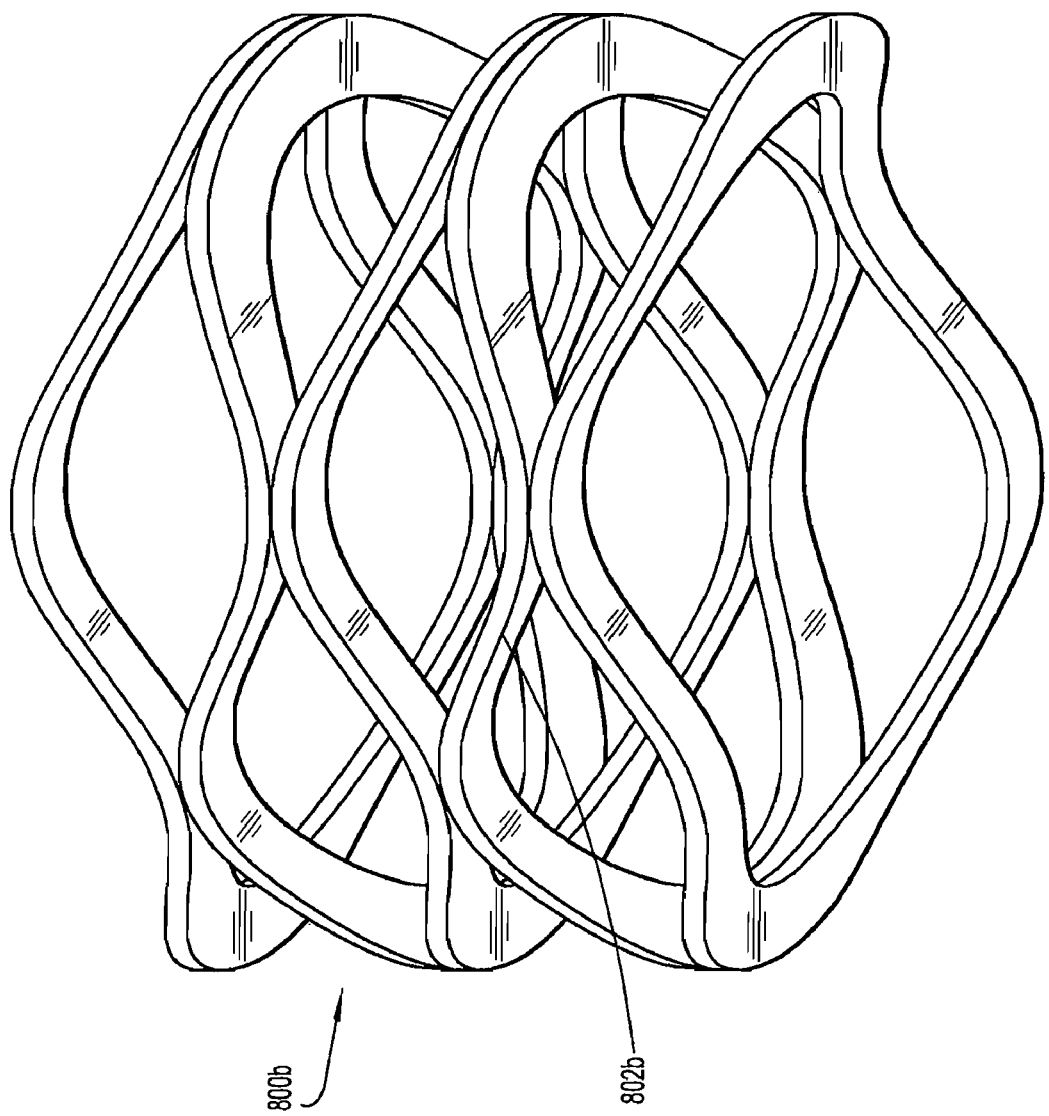

FIGS. 12A and 12B illustrate alternate springs such as wave spring 800a (FIG. 12A) and wave spring 800b (FIG. 12B) each of which may be substituted for coil spring 146 of the prior embodiments. Wave springs 800a, 800b provide advantages with respect to compressibility, restoration to its initial at rest position and reduced length, which may effectively permit a reduction in length of catheter hub 106. Wave spring 800a and wave spring 800b differ in the number of spring struts 802a, 802b as shown and thus provide different spring forces or constants. Other spring arrangements are also envisioned including tapered spring arrangements, bee-hive, hourglass, etc.

Figure 13:
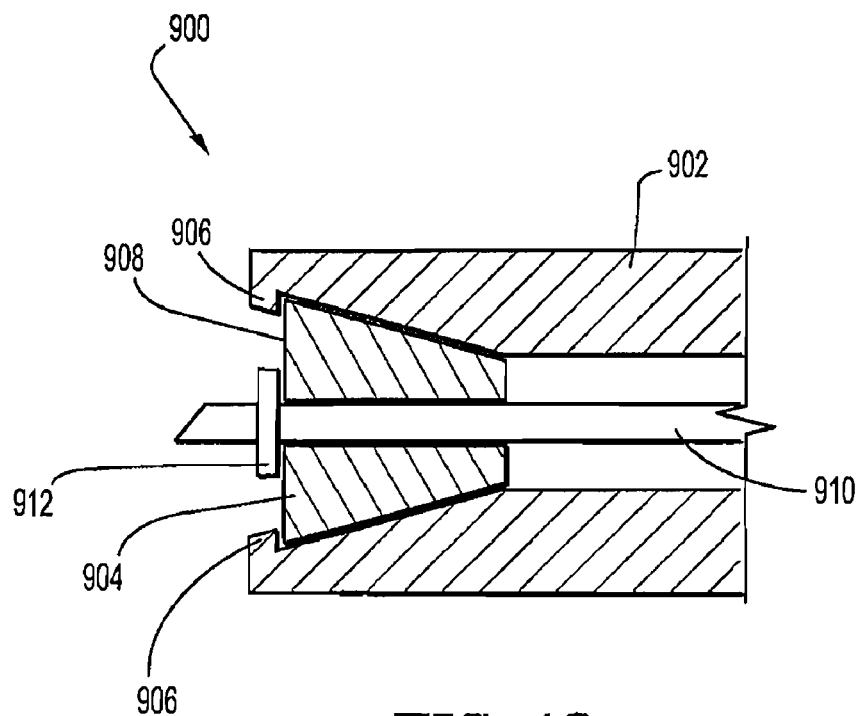
FIGS. 13-14 are side cross-sectional views of an alternate embodiment of a closure valve in the first and second positions, respectively.
Figure 14:
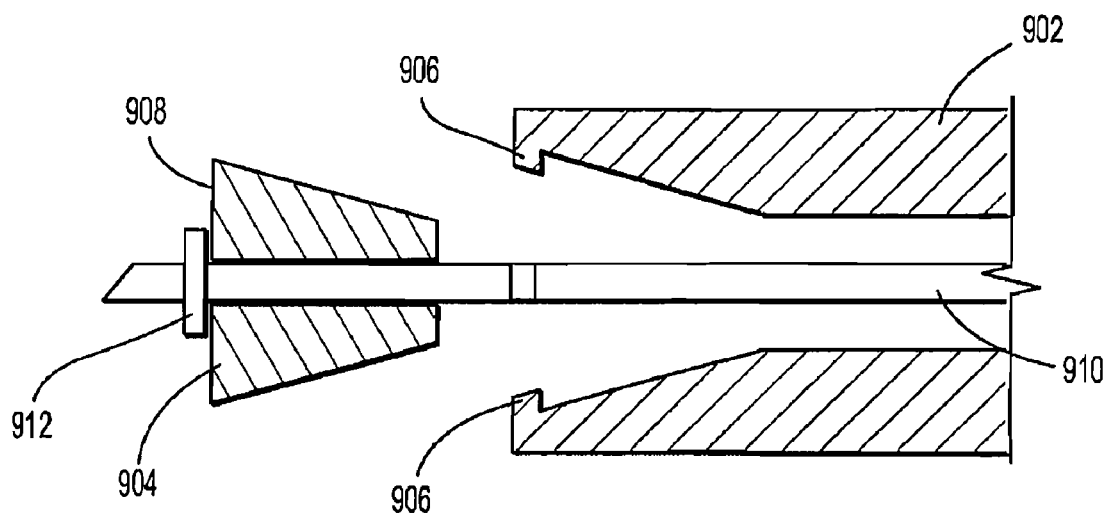

FIGS. 13-14 illustrate another embodiment of the closure valve for use with the transfer catheter of the present disclosure. Closure valve 900 includes valve housing 902 and internal access seal member 904 disposed within the valve housing 902. Valve housing 902 and access seal member 904 includes cooperating tapered configurations to position access seal member 904 in a closed condition in a similar manner to the methodology discussed hereinabove in the prior embodiments. Valve housing 902 further includes locking detents 906 depending radially inwardly from the periphery of the valve housing 902. Locking detents 906 serve to engage the distal face 908 of access seal member 904 to retain the access seal member 904 in the closed proximal position relative to valve housing 902 as depicted in FIG. 13. Access needle 910 may include locking ring 912 coaxially mounted about the access needle 910. Locking ring 912 engages the distal face 908 of access seal member 904 during withdrawal of the access needle 910 to move the access seal member 904 to the proximal position of FIG. 13. During this longitudinal movement, locking detents 906 deflect radially outwardly to permit passage of access seal member 904 whereby, upon clearance, the locking detents 906 return to the initial position of FIG. 13 in engagement with the access seal member 904. Access needle 910 may be removed from closure valve 900 and the transfer catheter. In one preferred embodiment, access seal member 904 has sufficient resiliency to permit locking ring 912 to pass through the access seal member 904 during withdrawal of the access needle 910. In other respects, closure valve 900 operates to open and close the fluid passage in a similar manner as described in the prior embodiments.

FIG. 15 illustrates an alternate embodiment of catheter hub 106 for use with transfer catheter 102 of the fluid transfer apparatus 100. Catheter hub 1000 is substantially similar to catheter hub 106 of the embodiment of FIG. 1, except for some variations in the design of the outer wall of catheter hub 1000. In addition, catheter hub 1000 includes a pair of wings 1002 in diametrical opposed relation extending radially outwardly from the catheter hub 1000. Wings 1002 facilitate securing of catheter hub 1000 to the subject with surgical tape, sutures, etc. as is known in the art.

FIGS. 16-17 illustrate an insertion stylet or needle 1100 which may be used in lieu of access cannula 104 of the fluid transfer apparatus 100 of FIG. 1. Insertion stylet 1100 may be solid along its length and preferably defines penetrating end 1102 having a general sharpened V-shaped configuration. Specifically, the V-shaped configuration is defined by plurality of intersecting surfaces 1104, 1106 which extends to a penetrating point or edge 1108. The intersections of surfaces 1104, 1106 and the lower surface (not shown) opposing surface 1106 define cutting edges 1110, 1112. The cross-section of insertion stylet 1100 proximal of penetrating end 1002 is preferably polygonal, e.g., hexagonal, in shape as shown in FIG. 17 to define a faceted appearance. With this arrangement, a plurality of channels 1114 is defined between the outer wall of insertion stylet 1100 and the inner wall of the elongated catheter member 1116. Channels 1114 permit fluid flow, e.g., blood flow, which may be visualized through catheter member 1116 (provided catheter member is at least partially transparent), e.g., flashback visualization, to identify entry of insertion stylet 1100 within the blood vessel. Alternatively, channels 1114 are in fluid communication with a flashback chamber associated with catheter hub 106 whereby the presence of blood in the flashback chamber identifies entry of insertion stylet 1100 within the blood vessel. In the alternative, channels 1114 may be associated with a sampling chamber to draw a sample of blood. In addition, elongated catheter member 1116 is shown as having beveled leading end surface 1118 to facilitate insertion within the tissue. In other respects, the fluid transfer apparatus incorporating insertion stylet 1100 functions in a similar manner discussed hereinabove in connection with the embodiment of fluid transfer apparatus 100 of FIGS. 1-3.

Figure 18:
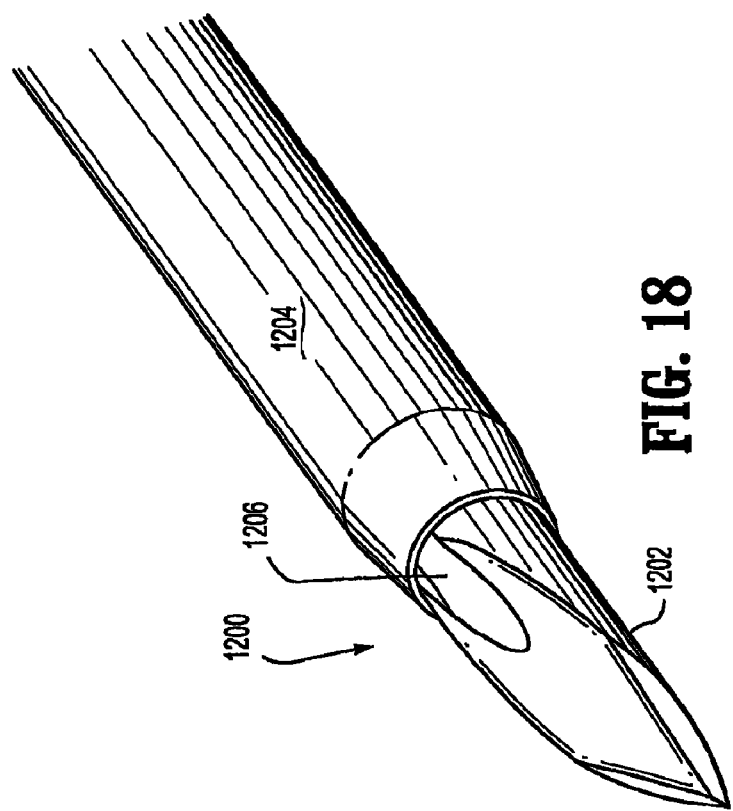
FIG. 18 is a perspective view of the penetrating end of an alternate insertion stylet for use with the fluid transfer apparatus of FIG. 1.

FIG. 18 illustrates an alternate embodiment of the insertion stylet 1100 of FIGS. 16-17. Insertion stylet 1200 includes penetrating end 1202 which is substantially similar to penetrating end 1102 of insertion stylet 1100 of FIGS. 16-17. The cross-section of insertion stylet 1200 proximal of penetrating end 1202 is substantially circular to generally correspond to the circular inner wall of elongated catheter 1204. Insertion stylet 1200 further defines external channel 1206 in its wall surface preferably extending along at least a portion of its length. External channel 1206 accommodates fluid flow, e.g., blood flow, to provide flashback visualization through elongated catheter 1204 or through a flashback chamber in a manner similar as discussed in connection with the embodiment of FIGS. 16-17. In other respects, fluid transfer apparatus incorporating insertion stylet 1200 functions in a similar manner to the embodiment of the fluid transfer apparatus 100 of FIGS. 1-3.

Figure 19:
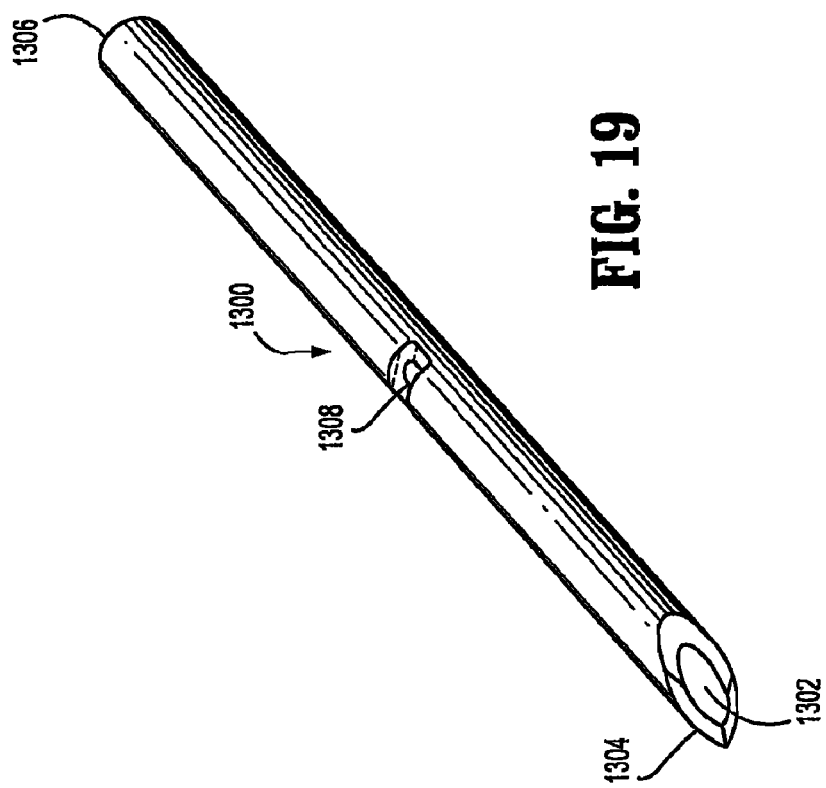
FIG. 19 is a perspective view of another alternate insertion stylet for use with the fluid transfer apparatus of FIG. 1.

FIG. 19 illustrates another alternate embodiment of an insertion stylet for use with fluid transfer apparatus 100. Insertion stylet 1300 functions as an access cannula similar to access cannula 104 of the fluid transfer apparatus 100 of the embodiment of FIGS. 1-3. Insertion stylet 1300 defines axial lumen 1302 extending through penetrating end 1304. However, the proximal or trailing end 1306 of insertion stylet is closed. Insertion stylet 1300 further defines opening 1308 adjacent an intermediate portion of insertion stylet 1300 in fluid communication with axial lumen 1302. When assembled, within fluid transfer apparatus 100, opening 1308 may be in fluid communication with a flashback chamber associated with catheter hub 106. Thus, fluid, e.g., blood, may be conveyed through axial lumen 1302 to exit opening 1308 and enter the flashback chamber.

Figure 20:
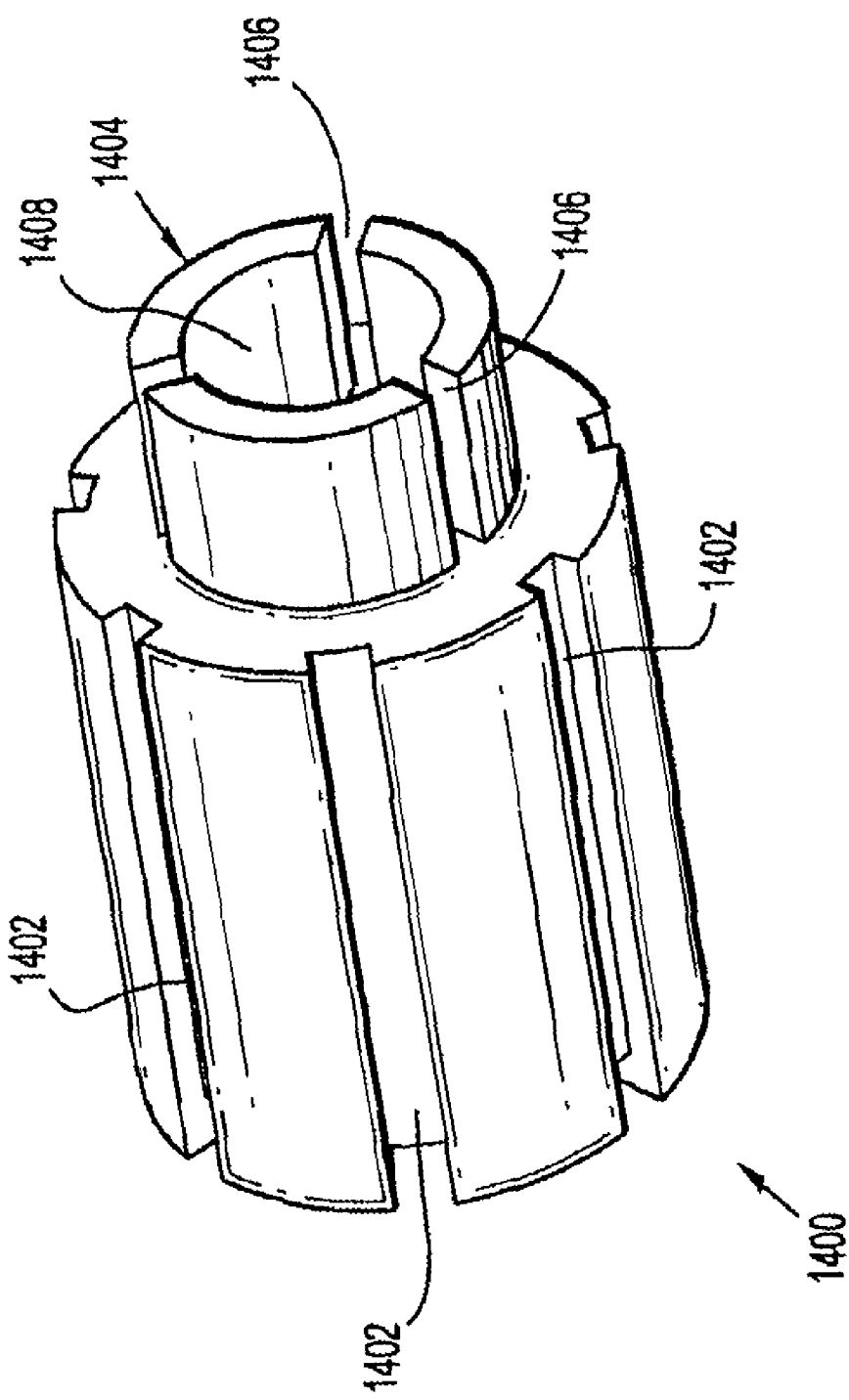
FIG. 20 is a perspective view of an alternate embodiment of a valve housing for use with the fluid transfer apparatus of FIG. 1.

FIG. 20 illustrates an alternate embodiment of valve housing 124 of fluid transfer apparatus 100 of FIGS. 1-3. Valve housing 1400 is similar to valve housing 124, but, further includes a plurality of radially spaced channels 1402 in its outer wall surface. Channels 1402 accommodate fluid flow about valve housing 1400 thereby defining at least a portion of the fluid passage "m" within catheter hub 106. Valve housing 1400 further includes valve plunger 1404 which extends proximally from the valve housing 1400. Valve plunger 1404 may be monolithically formed with valve housing 1400 or be integrally connected thereto. Valve plunger 1404 further defines one or more channels 1406 which extends through its wall in communication with internal lumen 1408 of the valve plunger 1404. Thus, upon connection to luer connector 200, fluid may be conveyed through internal lumen 1408 and channels 1406 of valve plunger 1404 and through channels 1402 of valve housing 1400 for delivery to the patient. In other respects, the internal structure and functioning of valve housing 1400 may be similar to corresponding structure and functioning of valve housing 124 of the fluid transfer apparatus 100 of the embodiment of FIGS. 1-3.

Figure 21:
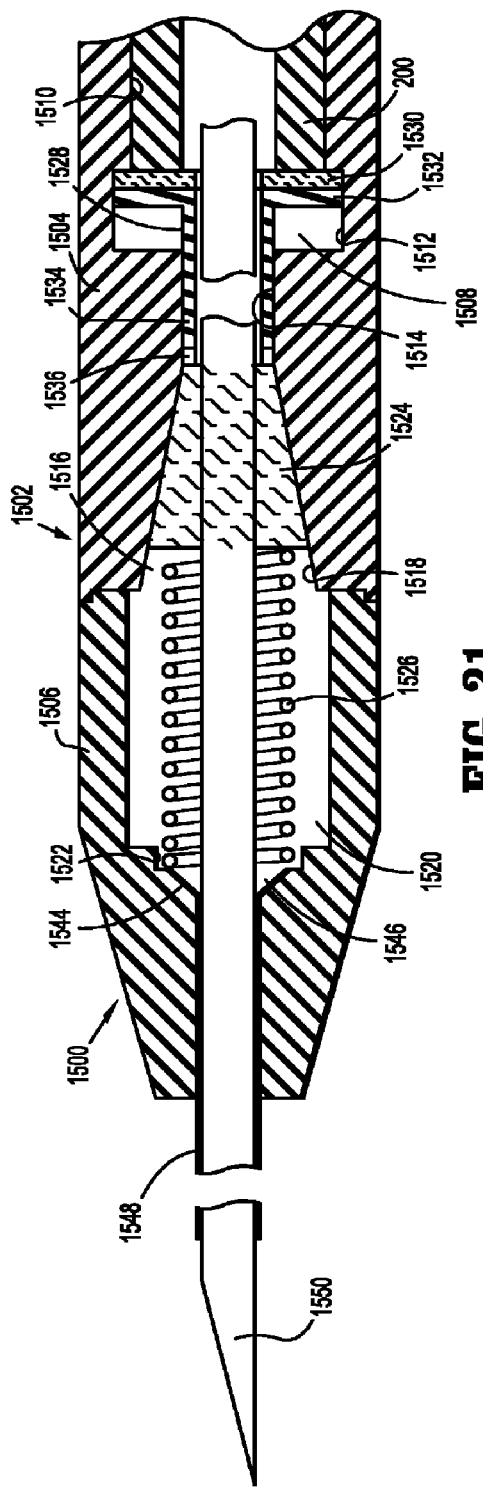
FIG. 21 is a side cross-sectional view of an alternate embodiment of the fluid transfer apparatus of FIG. 1 illustrating the transfer catheter and the access cannula positioned within the transfer catheter.
Figure 22:
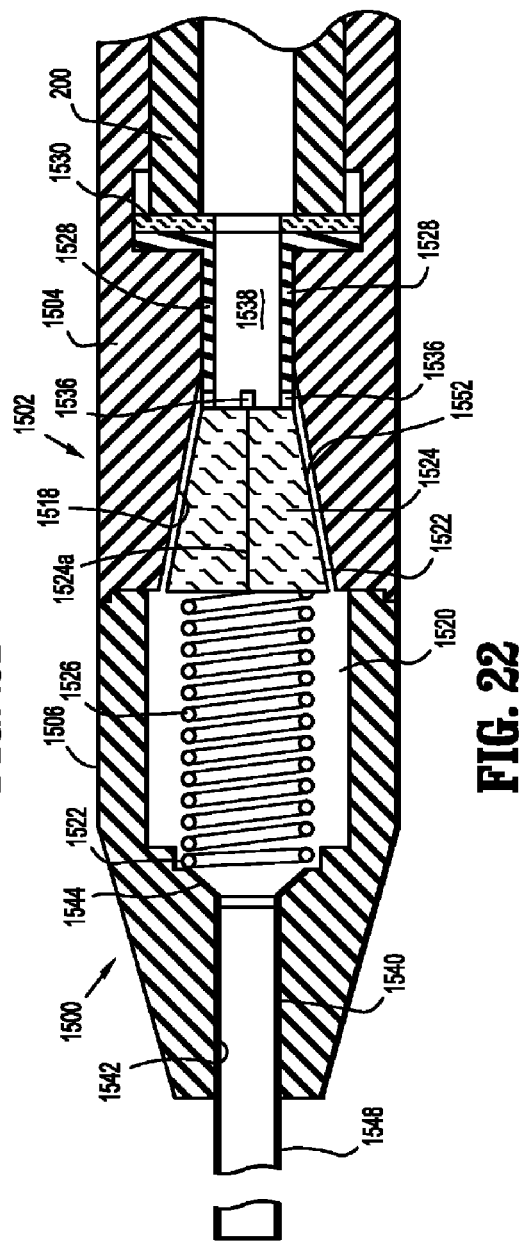
FIG. 22 is a side cross-sectional view of the fluid transfer apparatus of FIG. 21 with the access cannula withdrawn and a connector of a fluid distribution system mounted to the transfer catheter.
Figure 23:
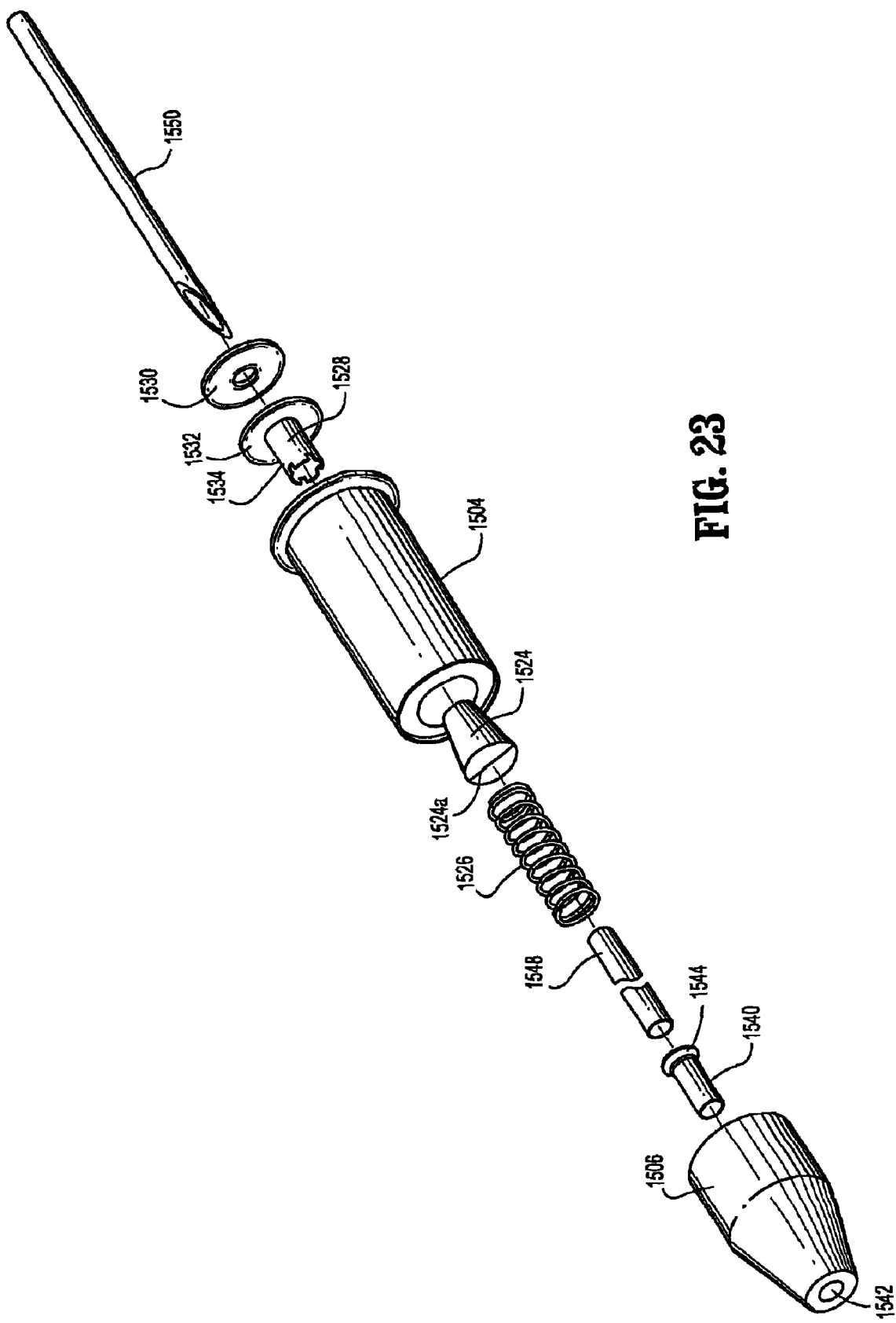
FIG. 23 is a perspective view with parts separated of the fluid transfer apparatus of FIGS. 21-22.

FIGS. 21-23 illustrate another alternate embodiment of the present disclosure. Fluid transfer apparatus 1500 is substantially similar to fluid transfer apparatus of FIG. 1, and, reference is made to the embodiment of FIG. 1 for a discussion of the structure and functioning of similar components. Fluid transfer apparatus 1500 includes catheter hub 1502 having first and second hub segments 1504, 1506 connected to each other via conventional means. Hub segment 1504 defines internal chamber or lumen 1508 having first chamber portion 1510 for reception of connector 200 of the fluid distribution system and second chamber portion 1512 defining an enlarged diameter relative to the first chamber portion 1510. Hub segment 1504 further defines linear bore 1514 of constant internal dimension or diameter adjacent second chamber portion 1512 and leading to tapered bore 1516. Tapered bore 1516 is defined within inner tapered wall 1518 of hub segment 1504. Second hub segment 1506 has fluid collection chamber 1520 and internal recess 1522 adjacent the leading end of the fluid collection chamber 1520.

Fluid transfer apparatus 1500 further includes closure valve 1524 at least partially disposed within tapered bore 1516 of hub segment 1504 and coil spring 1526 at least partially mounted within fluid collection chamber 1520. Coil spring 1526 normally biases closure valve 1524 to the initial position of fluid transfer apparatus 1500 depicted in FIG. 21. Coil spring 1526 is received, at its leading end, within internal recess 1522 and is thereby confined within the recess 1522. Closure valve 1524 and coil spring 1526 may be substantially similar to the corresponding components discussed in connection with the embodiment of FIG. 1.

Fluid transfer apparatus 1500 further includes valve plunger 1528 and valve gasket 1530. Valve plunger 1528 defines flange 1532 received within second chamber portion 1512 and plunger segment 1534 at least partially disposed in linear bore 1514. The diameter of flange 1532 generally approximates the internal diameter of second chamber portion 1512 of hub segment 1504. Plunger segment 1534 includes a plurality of recesses or openings 1536 in its wall adjacent the distal or leading end of the plunger segment 1534. Openings 1536 are in fluid communication with plunger channel 1538 extending through plunger 1528 to permit transfer of fluids. Valve gasket 1530 forms a substantial seal with the inner wall defining second chamber portion 1512 to minimize passage of fluids about plunger 1528.

Second hub segment 1506 has ferrule connector 1540 mounted within bore 1542 of hub segment 1506. Ferrule connector 1540 includes flange 1544 which resides within internal cavity 1546 of hub segment 1506. Flange 1544 of ferrule connector 1540 may be connected to second hub segment 1506 via conventional means including adhesives, cements, etc. Transfer catheter 1548 is secured to ferrule connector 1540 by conventional means and extends beyond second hub segment 1506 for positioning relative to the patient.

The use of fluid distribution system 1500 will now be discussed. With reference to FIG. 21, access cannula 1550 is positioned within first hub segment 1504, to pass through closure valve 1524 and transfer catheter 1548. During introduction, closure valve 1524 may move in a distal direction to permit slit 1524a of closure valve 1524 to open to receive access cannula 1550. Alternatively, closure valve 1524 may be formed of a highly conformable or resilient material whereby slit 1524a opens in response to the dimensioning of access cannula 1550 without any longitudinal movement of closure valve 1524. Access cannula 1550 is used to penetrate the blood vessel and is then removed. Upon its removal, closure valve 1524 assumes its normally closed position due, in part, to the biasing forces of coil spring 1526 and/or the resiliency of its material of fabrication.

With reference now to FIG. 22, luer connector 200 of, e.g., an IV system, is, then advanced within first chamber portion 1510 to contact valve gasket 1530 and drive valve plunger 1528 in a distal direction. Valve plunger 1528, in turn, drives closure valve 1524 distally to assume the activated position depicted in FIG. 22. In this position of closure valve 1524, an annular passage 1552 is formed between the periphery of closure valve 1524 and internal tapered wall 1518. Annular passage 1552 is in fluid communication with openings 1536 of valve plunger 1528, which, communicate with plunger channel 1538 of valve plunger 1528. The IV system may be activated whereby the therapeutic fluids pass from luer connector 200 through plunger channel 1538 to be distributed through openings 1536 of plunger 1528. The fluids are communicated through annular passage 1552 for reception within fluid collection chamber 1520 and subsequently distributed through transfer catheter 1548 and into the patient. Upon completion of therapy, connector 200 is removed, which thereby causes closure valve 1524, valve plunger 1528 and valve gasket 1530 to return to the normal condition depicted in FIG. 21 in response to the biasing forces of coil spring 1526.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical fluid transfer apparatus for passage of fluids, which comprises:
   a hub defining a longitudinal axis and having an internal chamber;
   an elongated member extending from the hub and defining a longitudinal conduit; and
   a closure valve disposed within the internal chamber of the hub, the closure valve adapted for longitudinal movement along the longitudinal axis between a first position substantially sealing the internal chamber to prevent passage of fluids and a second position establishing a fluid passage extending through the hub to permit passage of fluids therethrough and beyond the closure valve, the closure valve including a valve housing having inner wall portions defining a general tapered internal bore and a seal member at least partially disposed within the tapered internal bore of the valve housing, the seal member defining a general tapered configuration and having an open condition establishing an internal seal passage through the closure valve, the internal seal passage different than the fluid passage within the hub, the internal seal passage configured to permit passage of an access instrument through the closure valve and into the longitudinal conduit of the elongated member in substantial sealing relation with the access instrument, the seal member defining inner seal portions adapted for displacement to establish the seal passage to permit passage of the access instrument when in the open condition of the seal member and to establish the substantial sealing relation with the access instrument introduced therethrough, the seal member having a closed condition in the absence of the access instrument, the inner wall portions of the valve housing cooperating with the seal member to permit the seal member to assume the closed condition thereof, the fluid passage dimensioned and arranged to permit passage of fluids completely through the hub while the seal member is in the closed condition, the seal member adapted for longitudinal movement relative to the valve housing between an actuated position and an initial position corresponding to the open and closed conditions of the seal member.

2. The surgical apparatus according to claim 1 wherein the inner wall portions of the valve housing defining the tapered internal bore are adapted to cooperate with the seal member upon movement of the seal member to the initial position to substantially close the inner seal portions thereof.

3. The surgical apparatus according to claim 2 wherein the actuated position of the seal member is a distal longitudinal position and the initial position is a proximal longitudinal position.

4. The surgical apparatus according to claim 3 wherein the seal member is normally biased toward the proximal longitudinal position.

5. A surgical apparatus for passage of fluids, which comprises:
   a hub defining a longitudinal axis and having proximal and distal ends;
   an elongated member extending distally from the hub and defining a longitudinal conduit; and
   a closure valve mounted within the hub and adapted for longitudinal movement from a proximal position to a distal position, the closure valve including:
      a valve housing; and
      an internal seal member mounted to the valve housing, the internal seal member defining an internal passage through the closure valve, the internal seal member being adapted for longitudinal movement relative to the valve housing between a first position whereby the internal passage of the seal member is in a substantially closed condition and a second position whereby the internal passage of the internal seal member receives an access instrument, the internal seal member dimensioned and configured to establish a substantial sealing relationship with the access instrument;
   wherein the closure valve is dimensioned and arranged to establish a fluid passage extending completely through the hub upon movement of the closure valve to the distal position thereof, the fluid passage independent of the internal passage of the seal member.

6. The surgical apparatus according to claim 5 wherein the seal member is normally biased toward the first position thereof.

7. The surgical apparatus according to claim 6 wherein the seal member defines a general tapered configuration and is received within a corresponding tapered internal bore of the valve housing, the seal member cooperating with wall portions of the valve housing defining the tapered internal bore upon movement of the seal member to the first position to substantially close the internal passage of the seal member.

8. The surgical apparatus according to claim 7 wherein the valve housing is adapted to engage an internal sealing wall within the hub when in the proximal position of the closure valve to close the fluid passage.

9. The surgical apparatus according to claim 8 wherein the closure valve is normally biased toward the proximal position.

10. The surgical apparatus according to claim 9 including a spring engageable with the internal seal member to normally bias the internal seal member to the first position corresponding to a proximal position of the internal seal member relative to the valve housing, to thereby normally bias the closure valve to the proximal position thereof.

11. The surgical apparatus according to claim 9 wherein the valve housing includes a valve gasket, the valve gasket engaging the internal sealing wall when in the proximal position of the closure valve to close the fluid passage.

12. The surgical apparatus according to claim 6 wherein the fluid passage is dimensioned and arranged to permit passage of fluids through the hub while the seal member is in the first position.

* * * * *